(12) United States Patent
Windgassen et al.

(10) Patent No.: US 10,327,794 B2
(45) Date of Patent: *Jun. 25, 2019

(54) FORCEPS WITH A ROTATION ASSEMBLY

(71) Applicant: GYRUS ACMI, INC., Southborough, MA (US)

(72) Inventors: Ryan J. Windgassen, Nowthen, MN (US); Jeffrey Nelson, Maple Grove, MN (US); Dennis G. Lamser, Marlboro, MA (US); John R. Mensch, Plymouth, MN (US); Zane R. Ward, Prior Lake, MN (US); Timothy Ozell, Maple Grove, MN (US)

(73) Assignee: GYRUS ACMI, INC., Southborough, MA (US)

( * ) Notice: Subject to any disclaimer, the term of this patent is extended or adjusted under 35 U.S.C. 154(b) by 252 days.

This patent is subject to a terminal disclaimer.

(21) Appl. No.: 15/468,824

(22) Filed: Mar. 24, 2017

(65) Prior Publication Data
US 2017/0196580 A1 Jul. 13, 2017

Related U.S. Application Data

(63) Continuation of application No. 14/075,107, filed on Nov. 8, 2013, now Pat. No. 9,681,883.

(Continued)

(51) Int. Cl.
*A61B 17/29* (2006.01)
*A61B 17/295* (2006.01)
(Continued)

(52) U.S. Cl.
CPC ........ *A61B 17/2909* (2013.01); *A61B 17/295* (2013.01); *A61B 18/1445* (2013.01);
(Continued)

(58) Field of Classification Search
CPC ......... A61B 10/06; A61B 17/28; A61B 17/29; A61B 17/295; A61B 17/0467;
(Continued)

(56) References Cited

U.S. PATENT DOCUMENTS 5,425,743 A 6/1995 Nicholas
5,445,638 A 8/1995 Rydell et al.
(Continued)

FOREIGN PATENT DOCUMENTS

CN 101612053 A 12/2009
EP 2133028 A3 4/2013
(Continued)

OTHER PUBLICATIONS

Notice of Reason for Rejection, JP Application No. 2016-236492 dated Sep. 25, 2017.
(Continued)

*Primary Examiner* — David C Eastwood
*Assistant Examiner* — Erich Herbermann
(74) *Attorney, Agent, or Firm* — The Dobrusin Law Firm, P.C.

(57) ABSTRACT

A forceps comprising: (a) a stylet having a hollow tube having a proximal end region and a longitudinal axis; one or more assemblies that are extendable through the hollow tube, the one or more assemblies comprising: one or more support rods and one or more functional attachments; (b) a hand piece comprising: one or more housing structures defining a cavity; one or more actuating mechanisms comprising: a bearing fitting; a shuttle in communication with the bearing fitting constrained by a plurality of guide ridges; a socket housed by the shuttle; and one or more levers in communication with stylet so that movement of the one or more levers causes movement of the hollow tube and movement of the one or more assemblies; and wherein the (Continued)

movement of the hollow tube and the movement of the one or more assemblies are relative to each other.

20 Claims, 8 Drawing Sheets

Related U.S. Application Data

(60) Provisional application No. 61/796,411, filed on Nov. 9, 2012.

(51) Int. Cl.
*A61B 17/00* (2006.01)
*A61B 18/14* (2006.01)
*A61B 18/00* (2006.01)

(52) U.S. Cl.
CPC ........... *A61B 2017/00526* (2013.01); *A61B 2017/292* (2013.01); *A61B 2017/2913* (2013.01); *A61B 2017/2925* (2013.01); *A61B 2017/2929* (2013.01); *A61B 2018/00607* (2013.01); *Y10T 29/49826* (2015.01)

(58) Field of Classification Search
CPC ... A61B 17/32; A61B 17/3209; A61B 17/221; A61B 18/1445; A61B 2017/00526; A61B 2017/2913; A61B 2017/292; A61B 2017/2929; A61B 2017/2912; A61B 2017/2915; A61B 2017/2916; A61B 2017/2919; A61B 2017/2922; A61B 2017/2926; A61B 2017/2927; A61B 2017/2932; A61B 2017/2933; A61B 2017/2936; A61B 2017/2938; A61B 2017/2939
See application file for complete search history.

(56) References Cited

U.S. PATENT DOCUMENTS

| | | | |
|---|---|---|---|
| 5,458,598 A | 10/1995 | Feinberg et al. | |
| 5,462,546 A | 10/1995 | Rydell | |
| 5,483,952 A | 1/1996 | Aranyi | |
| 5,564,615 A | 10/1996 | Bishop et al. | |
| 5,647,871 A | 7/1997 | Levine et al. | |
| 5,735,849 A | 4/1998 | Baden et al. | |
| 5,766,166 A | 6/1998 | Hooven | |
| 5,810,805 A | 9/1998 | Sutcu et al. | |
| 6,190,386 B1 | 2/2001 | Rydell | |
| 6,270,497 B1 | 8/2001 | Sekino et al. | |
| 6,358,268 B1 | 3/2002 | Hunt et al. | |
| 6,679,882 B1 | 1/2004 | Kornerup | |
| 7,150,749 B2 | 12/2006 | Dycus et al. | |
| 7,377,902 B2 | 5/2008 | Burbank et al. | |
| 7,708,756 B2* | 5/2010 | Nobis | A61B 10/06 600/131 |
| 7,789,878 B2 | 9/2010 | Dumbauld et al. | |
| 8,328,802 B2 | 12/2012 | Deville et al. | |
| 8,425,511 B2 | 4/2013 | Olson | |
| 8,485,413 B2 | 7/2013 | Scheib et al. | |
| 8,491,626 B2 | 7/2013 | Roy et al. | |
| 8,523,898 B2 | 9/2013 | Bucciaglia et al. | |
| 8,535,312 B2 | 9/2013 | Horner | |
| 8,568,411 B2 | 10/2013 | Falkenstein et al. | |
| 2003/0229344 A1 | 12/2003 | Dycus et al. | |
| 2006/0084973 A1 | 4/2006 | Hushka | |
| 2008/0119870 A1 | 5/2008 | Williams | |
| 2009/0312773 A1 | 12/2009 | Cabrera et al. | |
| 2010/0023024 A1 | 1/2010 | Zeiner et al. | |
| 2010/0179540 A1 | 7/2010 | Marczyk et al. | |
| 2010/0198244 A1 | 8/2010 | Spivey et al. | |
| 2012/0022530 A1 | 1/2012 | Woodruff et al. | |
| 2012/0074200 A1 | 3/2012 | Schmid et al. | |
| 2012/0253344 A1 | 10/2012 | Dumbauld et al. | |
| 2013/0197552 A1* | 8/2013 | O'Brien, II | A61B 17/32002 606/170 |
| 2013/0267951 A1 | 10/2013 | Twomey | |
| 2013/0296922 A1* | 11/2013 | Allen, IV | A61B 18/1445 606/205 |

FOREIGN PATENT DOCUMENTS

| | | |
|---|---|---|
| JP | 2002-200087 A | 7/2002 |
| JP | 2016-236492 A | 8/2007 |
| JP | 2010-005386 A | 6/2009 |
| JP | 2010-068969 A | 4/2010 |
| WO | 94/16631 A1 | 8/1994 |
| WO | 01/66025 A1 | 9/2001 |
| WO | 2010/088588 A1 | 8/2010 |

OTHER PUBLICATIONS

Extended European Search Report, EP Application No. 18204226.7 dated Mar. 18, 2019.

* cited by examiner

FORCEPS WITH A ROTATION ASSEMBLY

FIELD

The disclosure relates to forceps with a member to facilitate axial movement and rotational movement of a gripping assembly, a cutting assembly, or both.

BACKGROUND

Generally forceps may be utilized for laparoscopic surgery. The forceps may be used to control delicate movements inside a patient. These forceps may be used to grip an anatomical feature. The forceps may include a gripping assembly or a cutting assembly. The forceps may include electrical energy for use in the gripping assembly. A user, in order to align the cutting assembly or to align the gripping assembly may have to rotate his or her arm to change the angle of the forceps to perform one of the functions of the forceps. A user while maintaining their arm in a rotated position may further be able to actuate the gripping assembly or the cutting assembly such that repositioning of one or more fingers and/or the user's hand may be required to simultaneously perform both functions. This simultaneous movement may cause the user to divert their attention from the anatomical feature of interest.

Current forceps during surgery may grip an item of interest to perform a surgical function thereon. Performing the surgical function with tools at the end of an elongated stylet may cause strain on the one or more support rods of the stylet. Strain on the one or more support rods may occur when the forceps are used to grip, cut, or perform another surgical function, and while performing the function the forceps are rotated by the user. Current forceps have intricate parts that make up assemblies and mechanisms. The intricate parts have precise placement requirements so that the intricate parts work together properly. These intricate parts during assembly may need one or more assemblies to be pre-assembled and/or manipulated once assembled such that the pieces may not be assembled in a single order without the need for reassembly of one or more of the previously installed components. The forceps include one or more levers that have a forked cam such that the levers cannot be installed without manipulating the one or more components they actuate.

Examples of some devices that may be used as a surgical instrument may be found in U.S. Pat. Nos. 5,735,849; 7,150,749 and Patent Application Publication No. 2003/0229344 all of which are incorporated by reference herein for all purposes. U.S. Pat. No. 5,735,849 discloses a forceps device that may work to cut or grip during surgery, but may not allow for simultaneous rotation and actuation of the cutting or gripping function. U.S. Pat. No. 7,150,749 discloses a forceps device that may work effectively to cut or grip during surgery, may not allow for rotation of the cutting or gripping assemblies without putting rotational strain on the support rod of the assemblies. U.S. Patent Application Publication No. 2003/0229344 discloses a forceps device that may work to cut or grip during surgery, may not be able to be assembled in a way where the parts may be placed into position without manipulating or repositioning other parts. It would be attractive for the forceps to move independently relative to the hand piece. What is needed is a bearing surface on the support rod of the one or more assemblies to allow for low friction rotation and longitudinal movement at the same time. What is needed is one or more levers configured to allow the device to be assembled along an assembly direction without repositioning of already installed components. It would be attractive to be have a device that may be robotically assembled. What is needed is a forceps that may be assembled by placing the parts into position without repositioning other parts so that the forceps may be assembled in a top-down manner.

SUMMARY

The disclosure meets one or more of the needs by providing: a forceps comprising: (a) a stylet having a distal end and a proximal end region, the stylet comprising; (i) a hollow tube having a proximal end region and a longitudinal axis; (ii) one or more assemblies that are extendable through the hollow tube, the one or more assemblies comprising; (1) one or more support rods having a distal end and a proximal end region; (2) one or more functional attachments at the distal end of the one or more support rods; (b) a hand piece comprising; (i) one or more housing structures defining a cavity that houses the proximal end region of the stylet; (ii) one or more actuating mechanisms in communication with the proximal end region of the stylet, the one or more actuating mechanisms comprising; (1) a bearing fitting located on the proximal end region of the stylet; (2) a shuttle in communication with the bearing fitting, the shuttle constrained by a plurality of guide ridges so that the shuttle is movable along a longitudinal axis and restricted from rotational movement around the longitudinal axis; (3) a socket housed by the shuttle, the socket receiving the bearing fitting so that the bearing fitting is rotatable relative to the shuttle; and (4) one or more levers in communication with stylet so that movement of the one or more levers causes movement of the hollow tube and movement of the one or more assemblies wherein the movement of the hollow tube and the movement of the one or more assemblies are relative to each other.

The disclosure provides: a surgical device comprising: (a) a stylet having a distal end and a proximal end; (b) a hand piece comprising: (i) one or more housing structures defining a cavity that houses the proximal end region of the stylet so that the stylet is assembled by being placed into the hand piece along an assembly direction; (ii) one or more actuating mechanisms in communication with the proximal end of the stylet, the one or more actuating mechanisms comprising; (1) one or more support rods having a distal end and a proximal end region, the proximal end region extending from the proximal end of the stylet; (2) one or more levers attached to one or more pivot axes in the hand piece, the one or more levers configured to form one or more slidable joints in communication with the one or more support rods so that movement of the one or more levers actuates the one or more slidable joints; wherein the one or more levers are configured to be assembled by: (1) being placed into the hand piece along the assembly direction before the stylet so that the stylet may be placed into the hand piece over the one or more levers; and (2) being placed into the hand piece along the assembly direction after the stylet so that the one or more levers is placed into the hand piece over the stylet, the one or more levers therefore being in communication with the stylet.

Additional embodiments comprise a method of assembling a device comprising: (a) providing a hand piece with a cavity; (b) assembling a stylet; (c) disposing a proximal end of the stylet into the cavity; (d) attaching one or more levers to the hand piece by one or more pivot axes so that part of the one or more levers is disposed within the cavity and part of the one or more levers extend out of the cavity;

and (e) connecting the one or more levers to the stylet; and wherein the one or more levers are attached to the hand piece before the stylet is attached to the hand piece so that the stylet is attached to the hand piece without repositioning of the one or more levers, or wherein the one or more levers are attached to the hand piece after the stylet is attached to hand piece so that the one or more levers are attached to the hand piece without repositioning of the stylet.

The teachings herein provide forceps that move independently relative to the hand piece. The teachings herein provide a bearing surface on the support rod of the one or more assemblies to allow for low friction rotation and longitudinal movement at the same time. The teachings herein provide one or more levers configured to allow the device to be assembled along an assembly direction without repositioning of already installed components. The teachings herein provide a device that may be robotically assembled. The teachings herein provide forceps that may be assembled by placing the parts into position without repositioning other parts so that the forceps may be assembled in a top-down manner.

DETAILED DESCRIPTION

Figure 1:
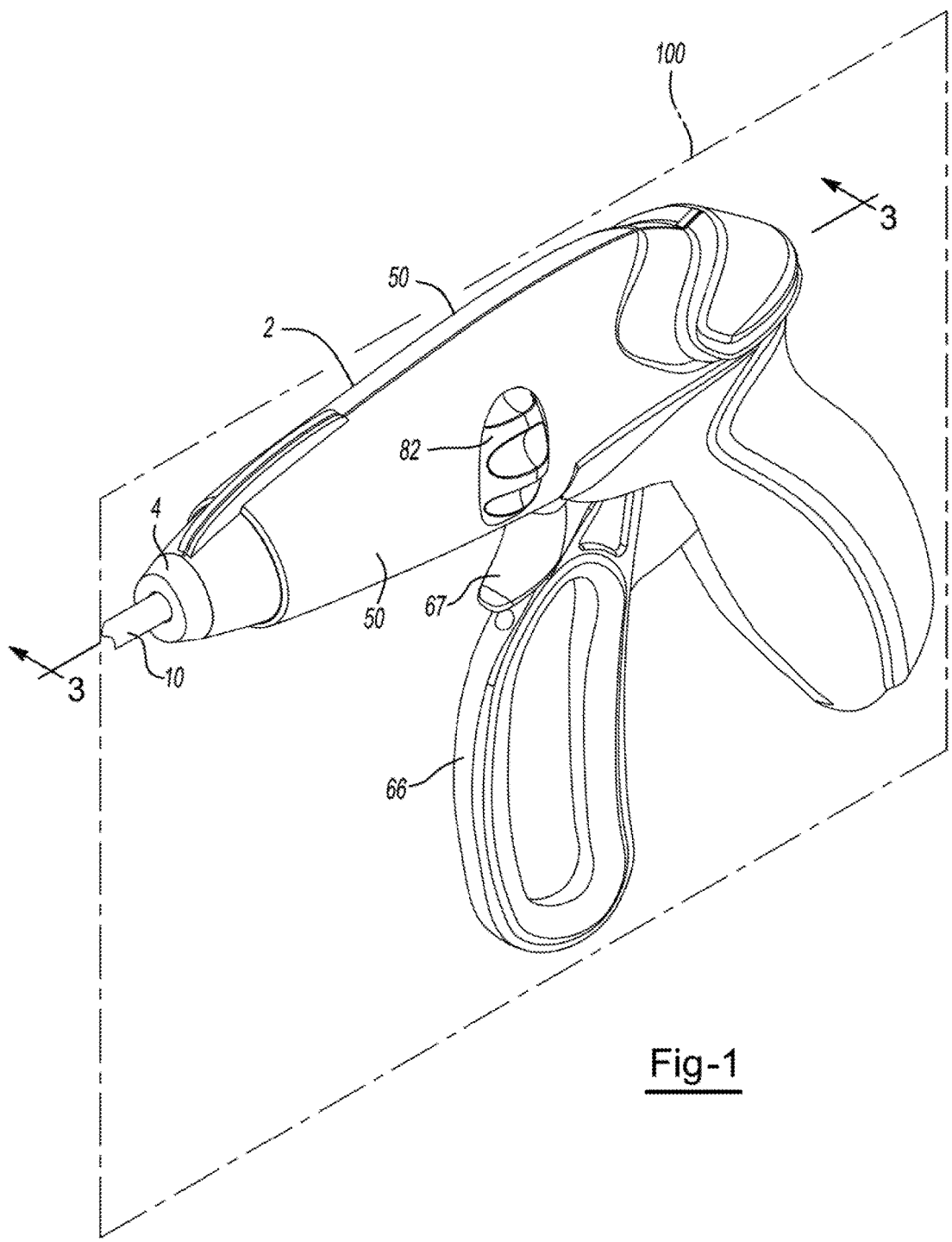
FIG. 1 illustrates a perspective view of one embodiment of the forceps device.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide a forceps device. The forceps may be any forceps that may grip an object. Preferably, the forceps may be used during surgery to grip a feature of interest including: a part of a body, an anatomical feature, tissue, veins, arteries, or a combination thereof. The forceps may be any forceps that may be used in surgery, for example laparoscopic surgery. The forceps may be used with or without power. Current may be passed through the forceps so that forceps are used for electrosurgery. For example, a therapy current may be passed from one jaw to a second jaw when tissue is located within the jaw and the therapy current may coagulate blood, cauterize, cut, or a combination thereof. The forceps may generally include one or more working assemblies and sufficient controls to work the one or more assemblies. The forceps may be comprised of parts needed to perform the recited functions and may include generally, a stylet, a hand piece, one or more levers used to actuate the stylet, or a combination thereof. The hand piece may be an assembly of parts or housing structures capable of forming a hand piece structure with a cavity. The stylet may be disposed in the cavity of the hand piece.

The stylet may be any device that extends into a patient during a surgical procedure so that a user can perform one or more surgical procedures. The stylet may be flexible so that the stylet may be moved within a patient. Preferably, the stylet may be substantially rigid so that the stylet may be moved to a desired location. The stylet includes a distal end and a proximal end. The distal end may be an end of the stylet that is located farthest from the hand piece. (e.g., the end of the stylet that is inserted into a patient). The proximal end of the stylet may be the end of the stylet located proximate to the user, in the hand piece, or both. For example, the proximal end may extend into the hand piece so that manipulation of the one or more levers manipulates the stylet. The stylet and its components may be made of any biocompatible material, for example, stainless steel, plastic, a synthetic material, a natural material, or a combination thereof. The stylet may comprise a stylet sub-assembly. The stylet sub-assembly may generally include one or more hollow tubes, one or more gripping assemblies, one or more cutting assemblies, one or more rotation mechanisms, one or more actuating mechanisms, or a combination thereof.

The one or more hollow tubes may function to house one or more working components (e.g., a gripping assembly, a cutting assembly, or both). The one or more hollow tubes may function to form an outer structure and support the stylet as the stylet extends outward from the hand piece. The one or more hollow tubes may be any device that may be used to extend a forceps device and any assemblies into a patient thereof. The one or more hollow tubes may assist in actuating a gripping assembly. The one or more hollow tubes may be a cannula. The one or more hollow tubes may be flexible. The one or more hollow tubes may include a curve, a bend, or a combination thereof. Preferably the one or more hollow tubes may be rigid. More preferably, the one or more hollow tubes are generally linear and are substantially rigid. The one or more hollow tubes may be any hollow tube shaped structure that may rotate around a longitudinal axis, its own longitudinal axis, or both. The one or more hollow tubes may include a distal end and a proximal end. The one or more hollow tubes may include an inner circumscribed diameter and an outer circumscribed diameter. The one or more hollow tubes may include a main body with a consistent inner and outer circumscribed diameter and a tapered portion with a larger outer circumscribed diameter than the main body. The tapered portion may be an overmolding affixed to the main body of the one or more hollow tubes. The tapered overmolding may be located at the proximal end of the one or more hollow tubes. The outer circumscribed diameter of the tapered overmolding portion of the one or more hollow tubes may increase suddenly at a shape angle, the outer circumscribed diameter may increase in a continuously changing slope or a gradual incline, the outer circumscribed diameter of the tapered portion may be stepped, or any combination thereof. The tapered overmolding may allow for the hollow tube to be actuated axially by making a contact point with the one or more control blocks. The one or more hollow tubes may be square, rounded, oval, irregular, or any shape that allows for the circumscribed diameter of the one or more hollow tubes to increase and that may allow for rotation around a longitudinal axis. The one or more hollow tubes may include an inner circumscribed diameter that assists in the functioning of the one or more assemblies.

The one or more hollow tubes may include an inner circumscribed diameter that may assist in rotation of the one or more assemblies. The one or more hollow tubes may include an inner circumscribed diameter that may assist on actuation of the gripping assembly. The one or more hollow tubes may include a constant inner circumscribed diameter, an inner circumscribed diameter that changes in the tapered portion, or a combination of both. The inner circumscribed diameter of the one or more hollow tubes may be any diameter so that one or more, and preferably two or more components may extend through a center (i.e., the hollow portion of the hollow tube) of the one or more hollow tubes for use during a surgical procedure, for example laparoscopic surgery. The inner diameter of the one or more hollow tubes may be sufficiently large so that the one or more hollow tubes may house the internal components and the internal components may be moveable into and out of the one or more hollow tubes (i.e., along a longitudinal axis of the one or more hollow tubes), radially within the one or more hollow tubes, rotationally within the one or more hollow tubes, or a combination thereof. The size of the inner diameter of the one or more hollow tubes may be sufficiently small so that camming sections extending radially from the proximal end of one or more opposing jaws are engaged by the hollow tube. The engaging of the radially extending camming sections may force the set of one or more opposing jaws or the functional attachment to bias (e.g., move towards each other to create a gripping force). The inner circumscribed diameter may be about 1 mm or more, preferably 3 mm or more, more preferably 5 mm or more. The inner circumscribed diameter may be about 20 mm or less, preferably about 15 mm or less, or more preferably about 10 mm or less. The inner circumscribed diameter may from about 1 mm to about 20 mm, preferably from about 3 mm to about 15 mm, or more preferably from about 5 mm to about 10 mm. The proximal end of the one or more hollow tubes may be disposed of in the hand piece. In the hand piece the one or more hollow tubes may extend through a return device and a stopping device.

The return mechanism may assist in actuating one or more assemblies. The return mechanism may return the one or more assemblies to neutral or resting position after actuation. The return mechanism may be any device that biases the hollow tube to resting position so that when the hollow tube is actuated and released from actuation the hollow tube returns back to resting position. The return mechanism may be a spring structure or any structure that can be compressed and released. The return mechanism may be a return spring. The return mechanism may use a stopping device support the return function.

The stopping device may be any device that may assist in actuating one or more assemblies. The stopping device may be any device that may assist in returning the one or more assemblies to neutral or resting position after actuation. The stopping device may act as a return mechanism anchor structure for the return mechanism. The stopping device may be any device that may allow for a return mechanism to remain stationary at one end while still applying force at the opposite end in the opposite direction, causing movement in that direction. The stopping device may be any shape that may allow the stopping device to be secured around a cylinder and be retrained from any movement. For example, the stopping device may be secured to the tapered overmolding portion of the hollow tube. The stopping device may be any structure that may remain secure around a cylinder and allow another piece to apply force to the stopping device without the stopping device moving. The stopping device may be a star washer. The stopping device may be secured to the proximal end of the tapered overmold portion of the one or more hollow tubes. The proximal end of the tapered overmold portion may have one or more tabs extending radially there from to be coupled with the control blocks.

The radially extending tabs may function to couple two or more devices together. The radially extending tabs may be any device that couples one or more control blocks. The radially extending tabs may be any device that allows for rotation of the one or more control blocks, longitudinally movement of the one or more control blocks along the stylet axis, or both. The radially extending tabs may be any structure that may allow for coupling with another structure. The radially extending tabs may be any structure that may allow for axial movement of the hollow tube while simultaneously being coupled with other structures. The radially extending tabs may be coupled to the one or more control blocks, the one or more control blocks preferably comprising a structure to couple to the tapered overmold portion. The tapered overmold portion of the one or more hollow tubes may be sufficiently long so that the radially extending tabs couple with the one or more control blocks. The radially extending tabs may allow for the one or more hollow tubes to be rotated when the user manipulates the structures coupled to the one or more hollow tubes.

The gripping assembly may function to create a gripping force, grip a feature of interest, or both. The gripping assembly may be one or more devices or parts that provide a gripping force, grips one or more objects, or both. The gripping assembly may be any combination of parts that may be used during surgery to grip one or more features of interest such as tissue, veins, arteries, an anatomical feature, or a combination thereof. The gripping assembly may be actuated by one or more levers. The gripping assembly may be used in surgery, for example laparoscopic surgery. The gripping assembly may create a sufficient gripping force so that one or more features of interest of a patient's body may be manipulated by the gripping assembly, secured by the gripping assembly, or a combination thereof. The gripping assembly may be composed of parts that may extend through the hollow tube. The gripping assembly may be an assembly of parts rotatable about an axis (e.g., a rotational axis of the gripping assembly, the longitudinal axis of the stylet, a longitudinal axis of the gripping assembly, or a combination thereof). The gripping assembly may grip and release while being simultaneously rotated. The gripping assembly may be actuated by the actuation mechanism in communication with the gripping assembly. The gripping assembly may be actuated by retracting the two opposing jaws into the one or more hollow tubes forcing the two opposing jaws closed. The gripping assembly may be actuated by extending the one or more hollow tubes away from the hand piece so that the one or more hollow tubes biases camming sections of the two opposing jaws towards one another into a closed position, creating a gripping force, or both. The gripping assembly may be any structure that may allow for top-down assembly. The gripping assembly may generally have two or more opposing jaws, and one or more jaw support rods, or a combination of both. Preferably, the gripping assembly may have two jaw support rods that each includes a camming section and an opposing jaw attached to each of the jaw support rods.

The two or more opposing jaws may function to perform a gripping function. The two or more opposing jaws may move towards each other to create a gripping force, to grip a feature of interest, or both. The two or more opposing jaws may be any devices that may be used to grip items of interest in surgery, for example laparoscopic surgery. The two or more opposing jaws may be any devices that may be used to grip or clamp an item of interest for cutting. The two or more opposing jaws may be any shape and size so that the jaws perform a gripping function, create a gripping force, or both. Preferably, the two or more opposing jaws may be one jaw structure with one opposing jaw structure that when forced together may allow for a gripping function. The two opposing jaws may be any two or more structures that may be movable relative to each other for perform a gripping function. The two opposing jaws may be any structures that may allow one jaw to be static and one jaw to be movable or any combination thereof. One or both of the two opposing jaws may include a pivot axis so that the two opposing jaws move about the pivot axis to perform a gripping function. The two opposing jaws may form a gap to allow for a cutting instrument to be inserted while retaining functionality of the two or more opposing jaws. The gap may be any shape and size so that a blade, functional element, a surgical instrument, or a combination thereof may be extended into the jaws, into the gap between the jaws, or both. The blade surgical instrument, functional element, or a combination thereof may be extended into the gap formed in (or between) the two opposing jaws while the two opposing jaws are closed, open, or a position there between. The two opposing jaws may be made of any material so that the two opposing jaws may be used to create a gripping force. The two opposing jaws may be made of a flexible material, resilient material, rigid stainless steel, a plastically deformable material, or a combination thereof. The two opposing jaws may be made of a material that conducts electricity. The two opposing jaws may apply the electricity to a feature of interest that may be gripped by the two opposing jaws. The gripping portion of the two opposing jaws may have a surface texture to grip a feature of interest. For instance the surface texture may be smooth, flat, contoured, serrated, textured, include ridges, mouse teeth, or a combination thereof. Preferably, the gripping portion of the two opposing jaws may have a serrated edge to allow for more secure gripping. The two opposing jaws may have an edge with a surface that may function similar to a serrated edge to allow for secure gripping. The two opposing jaws may be biased from an open position to a closed position by retraction of one of the one or more jaw support rods, movement of the one or more hollow tubes towards the distal end, or both along an axis of the one or more hollow tubes. The two opposing jaws may have laterally extending camming sections at the proximal end of the jaws that protruding out from the distal end of the hollow tube. Preferably, at least a portion of the laterally extending camming sections are wider than the mouth of the hollow tube so that axial movement of the hollow tube, the jaw support rods, or both biases the two opposing jaws closing the two opposing jaws, creating a gripping force, or both. For example, when a trigger is actuated the one or more hollow tubes may be moved towards (i.e., away from the hand piece) the two opposing jaws and may bias the two opposing jaws towards each other. The gripping assembly may be static relative to the hand piece so that once a feature of interest is placed between the two opposing jaws, the jaws may be biased to create a gripping force without having to reposition the two opposing jaws relative to the feature of interest. The gripping assembly may rotate in combination with the one or more hollow tubes, independent of the one or more hollow tubes, or both. Preferably, the gripping assembly may rotate independently of the hand piece. The griping assembly may rotate independently of the hollow tube. A proximal end of the two opposing jaws of the gripping assembly may each be attached to a one or more jaw support rods.

The one or more jaw support rods may function to assist a user in aligning a feature of interest between two or more opposing jaws, that may assist in creating a gripping force between the two opposing jaws, that may provide support to one or more jaws, extending through one or more hollow tubes, or any combination thereof. The one or more jaw support rods may be generally any shape that may perform the recited functions. The one or more jaw support rods may be any light weight material that is strong enough to support the two opposing jaws and to support the gripping action of the jaws. The one or more jaw support rods may be a solid cylindrical rod shape, the jaw support rod may be a hollow cylindrical rod shape, or both. The one or more jaw support rods may be flexible, rigid, conductive, elastically deformable, or a combination thereof. Preferably, the one or more jaw support rods may be a hollow tube. More preferably, the one or more jaw support rods may be a single jaw support rod. Most preferably, the one or more jaw support rods may each support a jaw. The one or more jaw support rods may be housed by a hollow tube of the teachings herein and may form a stylet. The jaw support rods may extend through the hollow tube at the distal end of the hollow tube at the proximal end of the hollow tube, or a combination thereof. The one or more jaw support rods may extend out of the distal end of the hollow tube and may have a functional attachment connected to the distal end of the one or more jaw support rods. The functional attachment may be one or both of two opposing jaws or an attachment with the functional equivalent of performing a gripping function. The proximal end of the one or more jaw support rods may extend from the proximal end of the hollow tube may be secured or fastened to a control block. The one or more jaw support rods may be secured to a spool control block, an anchor control block, or a combination thereof. The one or more jaw support rods may be actuated by the spool control block, the anchor control block, or both. The one or more jaw support rods may be adjacent to the cutting assembly inside the hollow tube.

The cutting assembly may be any assembly of parts capable of cutting. In general the cutting assembly may be any cutting assembly that may be used during surgery to cut tissue, veins, arteries, an anatomical feature, a feature of interest, or a combination thereof. The cutting assembly may be any cutting assembly that may be used in surgery, for example laparoscopic surgery. The cutting assembly may be any assembly of parts that may fit inside the hollow tube extend through the hollow tube, or a combination thereof. The cutting assembly may be any assembly of parts capable of rotating independent of the hollow tube or in combination with the hollow tube. The cutting assembly may be actuated to perform a cutting function by an actuation mechanism. The cutting assembly may be any cutting assembly that may generally be comprised of a blade, a blade support rod, or a combination thereof.

The blade may function cut a feature of interest. The blade may be any cutting tool that may be used in surgery, for example laparoscopic surgery. The blade may be any cutting device that may be extended and retracted through the hollow tube. The blade may be made of any material that may be sharpened; is strong enough to cut tissue, veins, arteries, an anatomical feature, a feature of interest, or a combination thereof; is biocompatible; that may conduct electricity; or a combination thereof. The blade may be any shape that may fit inside the hollow tube and extend into the gap formed between the two opposing jaws, so that a feature of interest for example an anatomical feature, tissue, veins, arteries, or a combination thereof may be cut. The blade may be sufficiently small so that the blade may be housed in the hollow tube during movement, insertion, or both. The blade may be extended into, and retracted from, the gap in the two opposing jaws. The distal end of the blade may have a shape edge. The proximal end of the blade may be attached to a blade support rod.

The blade support rod may function to support the blade and assist in moving the blade axially. The blade support rod may extend the blade out of the hollow tube, (e.g., into the gap formed by the two opposing jaws). The blade support rod may be any device that may retract the blade. The blade support rod may be extended or retracted by an actuating mechanism. The blade support rod may be used to actuate a blade in surgery, for example laparoscopic surgery. The blade support rod may be of shape and size to actuate a blade inside a hollow tube. For example the blade support rod may be a wire, shaped metal, rod, a plurality of combined longitudinal pieces, or any similar rigid structure that may fit in and extend through the hollow tube. The blade support rod may be made of a material that is light weight, but strong enough to extend a blade through a feature of interest, for example, an anatomical feature, tissue, veins, arteries, or a combination thereof; thereby cutting the feature of interest. The blade support rod may have a distal end and a proximal end. A blade may be attached to a distal end, a distal end region, or both of the blade support rod. The blade support rod may have a structure at the proximal end of the blade support rod, at the proximal end region of the blade support rod, or both to assist in rotation of the blade. The blade support rod may have a bearing fitting structure affixed to the proximal end region of the blade support rod. The blade support rod may extend through the bearing fitting structure and may extend through a shuttle housing the bearing fitting structure. A portion of the blade support rod may have a stopping feature to restrain longitudinal movement along a longitudinal axis, the stopping feature may include a shoulder structure, a tapered feature, or both that may prevent the blade support rod from axially moving through the bearing fitting. The blade support rod may be in communication with the actuating mechanism. The blade support rod may be in communication with the actuating mechanism inside a hand piece.

The hand piece may be any device that forms an enclosing structure for the forceps. The hand piece may be any device that houses the working assemblies and parts of the forceps. The hand piece may be any device that houses the controls to work the assemblies of the forceps. The hand piece may be comprised of one or more housing structures. Preferably, the hand piece is two or more housing structures. The hand piece may be an assembly of parts or housing structures that when combined form a hand piece structure. The hand piece may be any structure that is gripped by a user. The hand piece may be any structure that combines one or more of the components discussed herein so that forceps are formed. The hand piece may be any structure that may assist in performing laparoscopic surgery. The hand piece may be ergonomically shaped. The ergonomic shape of the hand piece may be any shape so that the forceps may be used ambidextrously. The ergonomic shape of the hand piece may be any shape such that all the controls can be accessed by a single hand gripping the hand piece. The hand piece may have a bisecting plane to define an assembly direction. The hand piece may be comprised of housing structures.

The housing structures may be any devices that form the hand piece. The housing structures may be any devices that may affix certain pieces into position. The housing structures may form a cavity to house working assemblies of the forceps. The housing structures may be one or more housing structures and preferably two or more housing structures. The housing structures may be any devices that include a recess for receiving one or more components of the forceps, the hand piece, or both. The two housing structures may be bisected by a plane that extends through the two housing structures so that a substantially equal and/or mirror image housing structure is located on each side of the plane. For example, the plane may extend through the longitudinal axis of the stylet and parallel to the walls of both housing structures so that the housing structures extend along each side of the plane. The plane may separate and define a left portion and a right portion when the device is oriented in an upright position. The plane may separate and define a bottom portion and a top portion when the device is oriented in a flat position and lying on its side. The plane that bisects the hand piece may determine an assembly direction normal to the plane. The plane that bisects the hand piece may extend through the hand piece along the longitudinal axis of the stylet. The hand piece may house a power cord used to integrate power into the gripping assembly. The housing structures of the hand piece may include a web structure. The web structure is a plurality of forms extending from the inside surface of the housing structures. The web structure may hold the inner parts of the forceps in place to assist in assembly of the forceps and to assist in the proper functioning of the parts of the forceps. The web structure may house parts of the one or more assemblies, form attachment points for one or components of the assembly and/or forceps, or both. The web structure may house the control blocks, a rotation wheel, or a combination thereof. The housing structures may have one or more guide ridges attached. The one or more guide ridges may be any form or structure attached to the housing structure that may act as a guide for other moving parts. The one or more guide ridges may be any form or structure that may allow for a shuttle device, or similar structure to move axially and at the same time be restrained from any rotation. The one or more guide ridges may house one or more parts of the actuation mechanism. The one or more guide ridges may house and restrain a shuttle. The housing structures may include one or more structures that may act as one or more pivot axes. The one or more pivot axes may receive the one or more levers, and may restrain the movement of the one or more levers to only axial movement around the one or more pivot axes. The housing structures may be secured at the distal end where the stylet enters the hand piece by a nose cone that connects the housing structures together. The housing structures may house an actuating mechanism.

The actuating mechanism may function to actuate another structure or assembly. The actuating mechanism may be any mechanism capable of actuating the gripping assembly, the cutting assembly, or both. The actuating mechanism may actuate one or more control blocks, a shuttle, or both. The actuating mechanism may be in communication with the proximal end, a proximal end region, or both of the gripping assembly, the cutting assembly, or both. The actuating mechanism may be controlled and actuated by the user's hand or fingers. The actuating mechanism may generally include one or more control blocks, a bearing fitting, a shuttle with a socket and a travel pin, or a combination thereof.

The one or more control blocks may function to secure one or more of the assemblies in the stylet. The one or more control blocks may be any device that actuates the one or more assemblies. The one or more control blocks may be a structure that rotates the one or more assemblies. The one or more control blocks may rotate independently, or in combination with the one or more assemblies. The one or more control blocks may move longitudinally relative to each other along a longitudinal axis. The one or more control blocks may be coupled to each other, to a rotation wheel, to the hollow tube, or any combination thereof. The one or more control blocks may generally be a spool control block or an anchor control block.

The one or more spool control blocks may function to assist in actuation or rotation, or both, of the one or more assemblies. The one or more spool control blocks may be any device that may slide longitudinally over an anchor control block and simultaneously be coupled to the anchor control block for rotation. The spool control block may be secured or restrained by web structures in the hand piece. The one or more spool control blocks may be any size and shape so that the spool control block may fit around the anchor control block, and so that the spool control block may actuate the one or more assemblies. The spool control block may be generally any shape and size required to perform the recited functions, for example cylindrical and hollow shaped so that the spool control block may rotate around the longitudinal axis of the stylet. The spool control block may have one or more grooves on the inside surface. The one or more grooves may match up with one or more fins extending from the outside surface of the anchor control block to allow coupling. The spool control block may have one or more tabs extending radially from the outside surface of the spool control block. The outside of the spool control block may be coupled with a rotation wheel to allow rotation and longitudinal movement along a longitudinal axis. The spool control block may have a shoulder at the proximal end of the spool control block. The shoulder may be any structure that may act as a point of contact for the actuation mechanism to actuate the spool control block and anything secured by the spool control block. The shoulder may be formed by an extension protruding from the proximal end of the spool control block, the extension having a smaller diameter than the main body of the spool control block. The shoulder may allow for the one or more levers to actuate spool control block. The control anchor block may be connected to the jaw support rod with the hollow tube being secured to the housing. Moving the one or more levers may cause the hollow tube to advance with respect to the jaw support blade. Moving the lever may cause the jaw support rod to be retracted into the tube. The hollow tube may be static to the hand piece and the jaw support rod may be rotatable round the longitudinal axis. Preferably, the spool control block may be attached at its distal end to the proximal end of the hollow tube. The spool control block may be slidable over the anchor control block so that is may actuate the hollow tube attached at the distal end of the spool control block. Actuation of the hollow tube may cause the two opposing jaws to close and to perform a gripping function. The spool control block may rotate the hollow tube when the hollow tube is attached. The spool control block may rotate the one or more assemblies and the anchor control block.

The anchor control block may function to assist in actuating or rotation of the one or more assemblies. The anchor control block may secure the one or more jaw support rods. The anchor control block may house the one or more blade support rods. The anchor control block may be any structure that may assist in actuation of the one or more assemblies. The anchor control block may be any structure that assists in rotating the one or more assemblies. The anchor control block may be any structure that may slide inside of the spool control block and simultaneously be coupled to the spool control block. The anchor control block may be any structure that may secure the one or more assemblies. The anchor control block may be any structure that may allow for the one or more assemblies to rotate simultaneously. The anchor control block may be solid and may have a smaller diameter than the spool control block. The anchor control block may be static while the spool control block slides over the outside of the anchor control block. The anchor control block may secure the proximal ends of the jaw support rods, the proximal end of the hollow tube, or a combination thereof. The anchor control block may have a main body portion on the distal end region of the anchor control block. The anchor control block may have a circumferential groove at its proximal end. The circumferential groove of the anchor control block may be placed into contact with a web structure in the housing structure so that the web structure restrains the anchor control block to prevent axial movement and allow for axial rotation. The main body of the anchor control block may have one or more fins extending laterally from the outside surface. The one or more fins may be coupled with the one or more grooves on the inside surface of the spool control block. The anchor control block and the spool control block may be coupled so that rotational movement of the spool control block causes rotational movement in the anchor control block. A blade support rod may extend through the anchor control block into the hand piece. The portion of the blade support rod extending through the anchor control block may extend through a bias device and into a bearing fitting.

The bias device may function to assist in returning one or more assemblies to the neutral or resting position after being actuated. The bias device may be any device that will act to return the blade support rod back into the neutral position after the blade support rod is actuated. The bias device may accept force applied by a piece of the forceps and apply the same force back on the piece to return it to the original position. The bias device may be any shape and size to fit over the blade support rod and into the one or more guide ridges. The bias device may be any structure that may be attached to the shuttle and the housing structure to return the shuttle to neutral or resting position. The bias device may be any device that may function as a spring, for example a compression spring or an extension spring. The bias device may be a structure that may be rigid enough to withstand pressure when pressure is applied. The bias device may be any structure that is flexible enough to be bendable without breaking and that can be manipulated and returned back to form of the structure before manipulation. The blade support rod may extend through the bias device and into a bearing fitting.

The bearing fitting may function to assist in rotation and actuation of the one or more assemblies. The bearing fitting may rotate with the one or more support rods inside of a socket housed by a shuttle. The bearing fitting may be any device that receives force from the socket and shuttle and is rotational at the same time. The bearing fitting may assist in allowing for low friction rotation between two surfaces. The bearing fitting may be any structure that may be moved axially and that may be rotatable at the same time. The bearing fitting may be any structure capable of being moved by socket housed by a shuttle. The bearing fitting may be attached at the proximal end, or proximal end region of the blade support rod. The bearing fitting may be made from any material allowing for smooth rotation. The bearing fitting may have a generally axisymmetric outer surface, or any shaped surface that may allow for rotation of the blade support rod around a longitudinal axis. The bearing fitting may be attached, crimped, or connected to the blade support rod in any manner that would cause the bearing fitting to be secured to the blade support rod. The bearing fitting may be static to the blade support rod, or the bearing fitting may be capable of rotation around the axis of the blade support rod. The bearing fitting may be of any size smaller than the shuttle so that the bearing fitting may be received inside of a socket housed by a shuttle and moved by the shuttle.

The shuttle may be any device that actuates one or more assemblies. The shuttle may be any device that actuates one or more assemblies when the shuttle is moved by one or more levers. The shuttle may house a socket which receives the one or more support rods. The shuttle may be any structure that may actuate a support rod. The shuttle may be any structure that may actuate a bearing fitting attached to the end of a support rod. The shuttle may convert angular force provided by the one or more levers into linear force moving the one or more assemblies longitudinally along a longitudinal axis. The shuttle may be any device that moves longitudinally along an axis without rotation. The shuttle may be any shape or size necessary to perform the recited functions. The shuttle in general may be cubed shaped, cylindrical shaped, or any shape that may allow the shuttle to be placed over a bearing fitting and into a plurality of guide ridges formed in the housing structures. The shuttle may be any shape that may be restrained from axially moving by the plurality of guide ridges. The shuttle may be any shape that may allow for the bearing fitting to be housed by the socket. The socket housed by the shuttle may be any shape and size necessary to allow for low friction rotation between the shuttle and the support rod. The socket may have an axisymmetrical design inside the shuttle where the socket receives the bearing fitting or support rod. The shuttle may be in contact with the bearing fitting or the shuttle and the bearing fitting may be spaced apart. The spatial relationship between the socket and the bearing fitting surface, being together or apart, may allow for low friction rotation between the bearing fitting and the shuttle. The shuttle may be actuated by one or more levers having a cam finger or camming slot. The one or more levers may be in communication with a travel pin extending laterally from the shuttle.

The travel pin may be any device that assists in actuating the shuttle. The travel pin may be any device that provides a contact point for the one or more levers. The travel pin may convert the movement of the one or more levers to movement of the shuttle. The travel pin may be any structure that moves the shuttle by applying directional force to the shuttle. The travel pin may be any structure that may be moved by a camming slot at the end of one or more levers. The travel pin may be any shape that may allow for the travel pin to move inside of a curved or arcuate camming slot. The travel pin may be any shape that may allow for the travel pin to create a gripping force in a groove, slot, hole, or any other area the travel pin may fit in. The travel pin may have a sufficient length so that the travel pin may form a connection with the one or more levers, and so that the travel pin may be received by a camming slot. The travel pin may extend through the camming slot and may be secured by one or more guide ridges in the housing structures. The shuttle may be actuated by applying a directional force to the travel pin. Shifting and rotating of the shuttle may not allow the shuttle to move axially without getting stuck. The directional force on the travel pin may cause the shuttle to shift and rotate unless that is a reason why it can only go one way. The one or more guide ridges may act as a reason for the shuttle to move in one way, axially. The one or more guide ridges on the one or more housings may allow the shuttle to receive a force from the one or more levers on the travel pin on one side of the shuttle and may allow for axial movement of the shuttle along a longitudinal axis without getting stuck. The shuttle, the socket, and the bearing fitting may be actuated by one or more levers.

The one or more levers may be any device manipulated or moved by applying pressure to a portion of the one or more levers with a hand or fingers. The one or more levers may be any device that may bias other moveable components, for example the hollow tube, a cutting assembly, a blade assembly, a functional assembly, or a combination thereof. The one or more levers may be biased ambidextrously. The one or more levers may be any structure that can pivot around a pivot axis. The one or more levers may be any structure that may allow for the one or more levers to be in communication with the one or more assemblies in the stylet. The one or more levers may be any structure that may allow for the one or more levers to actuate the one or more assemblies in the stylet. The one or more levers may be a single lever that may be link to two different functions and may be biased to generate each function individually or simultaneously. The two different functions linked may be the function of actuating the cutting mechanism and the function of actuating the gripping mechanism. The single lever that may link two functions may have a hinge in the single lever that separates two portions of the lever. The hinge may allow for a portion of the single lever to be moved relative to the other portion of the lever. Preferably, the one or more levers may be a two levers and each lever may be biased to perform a different function. The two levers may be a clamp lever and a cut trigger lever. The combination of two levers may include a forked two-sided cam finger, a yoke, or a combination thereof. Preferably, each of the two levers may include an arm with a camming slot extending from the one or more levers, a single cam finger, or two-sided cam finger or yoke extending from the one or more levers, or a combination thereof.

The two-sided cam finger or yoke may function to actuate the one or more assemblies. The two-sided cam finger or yoke may be any device assembled in a top down assembly direction by fitting the two-sided yoke onto the stylet. The two-sided cam finger or yoke may be placed in communication with the stylet while the one or more levers are in a perpendicular angle to the stylet. The one or levers that are perpendicular to the stylet are placed in communication with the stylet along the primary assembly direction. Once the two-sided cam finger or yoke is placed over the stylet so that the stylet may fit in between the two fingers of the two-sided cam finger or yoke, the one or more levers may be rotated so the one or more levers are perpendicular to the assembly direction. The degree rotation of the one or more levers is the amount necessary to move the one or more levers along a secondary assembly direction so that the one or more levers are in the proper position. Rotating the one or more levers once placed in communication with the stylet may allow for the one or more levers to be assembled along with the stylet in a top-down assembly direction.

The assembly direction may be the direction of assembly that is referred to in this application herein. The assembly direction may be a direction along a line normal to a plane bisecting the hand piece. The assembly direction may be a line that is perpendicular to the bottom portion housing structure where the pieces of the forceps device are placed into position. The primary assembly line may be the assembly direction followed to attach the one or more levers having a two-sided cam finger or yoke to the stylet sub-assembly. The secondary assembly direction may be a rotational line where the one or more levers having a two-sided cam finger or yoke are rotated to be properly aligned in the hand piece. The secondary assembly direction may be any direction where a part may be rotated once in communication with the forceps. The rotation may be to the degree necessary to align the part with all pieces in communication with the rotated part.

The one or more cam fingers may function to assist in actuating one or more assemblies. The one or more cam fingers may convert an arched force of motion created by the one or more levers to a linear force of motion causing the shuttle to actuate the one or more assemblies. The one or more cam fingers may be any structure that extends upwardly from the one or more levers and makes contact with the one or more control blocks. The one or more cam fingers may be any structure that may push the spool control block and that may cause the spool control block to move axially. The one or more levers and the one or more cam fingers may be used to actuate the actuating mechanism. The one or more cam fingers may be moved by manipulating the one or more levers on a pivot axis point with the user's hand or fingers. The one or more cam fingers may actuate the spool control block by applying force to the spool control block at a single contact point. The one or more cam fingers may be positioned so that the one or more cam fingers is only located on one side of a plane as discussed herein that bisects the hand piece. The one or more cam fingers may actuate the gripping assembly without the need for a forked cam finger or a two-sided yoke. one or more cam fingers may be in communication with one side of the extension protruding from the proximal end of the spool control block. The one or more cam fingers may be placed into position in the hand piece along the assembly direction without manipulating or repositioning the control block or any part of the stylet sub-assembly. The one or more levers with the one or more cam fingers may be placed into position in the hand piece along the assembly direction before the stylet sub-assembly so that the stylet sub-assembly may be placed into the hand piece without manipulating or repositioning the one or more cam fingers and the one or more levers.

The one or more levers may include an arm. The arm extending from the one or more levers may be any device that assists in actuating the one or more assemblies. The arm may be any device that converts the arched motion of the one or more levers into a linear motion of the one or more assemblies. The arm may be any shape or size to perform the recited functions. The arm may be any structure that may pivot around a pivot axis so that the movement of the one or more levers causes the movement of the arm in the opposite direction of the movement of the one or more levers. The arm may be any structure that may receive the travel pin and that may apply directional force to the travel pin. The arm may be any structure that may have a groove, slot, hole, or other shape to receive the travel pin and move the travel pin axially. The arm may extend from the one or more levers and may have a camming slot in the region of the extending arm. The camming slot may receive a travel pin. The camming slot may be any slot with a shape, which acts to convert the arched direction of the force produced by fingers manipulating the lever into a linear direction of force applied to the travel pin extending from the shuttle. The arm extending from the one or more levers may be on one side of the plane that separates or defines the two housing structures of the hand piece. The arm extending from the camming slot may receive the travel pin and be in communication with one side of the shuttle of the cutting assembly. The arm with the camming slot may be placed into position in the hand piece without manipulating or repositioning the travel pin, the shuttle, or any part of the stylet assembly already in the hand piece. The travel pin, shuttle and the rest of the stylet assembly may be placed into the hand piece after the one or more levers with an arm and camming slot so that the stylet assembly is placed in communication with the camming slot of the arm without manipulating or repositioning the arm with the camming slot one or more levers, or both. The arm with the camming slot extending from the one or more levers may actuate the cutting assembly by causing the camming slot to move the travel pin and the shuttle so that the pushrod is moved to create a cutting action, therefore moving the cutting assembly.

The stylet may include a rotation mechanism. The rotation mechanism may be any assembly of parts that may rotate the one or more assemblies. The rotation mechanism may be any assembly of parts that may rotate, and allow for actuation of the one or more assemblies. The rotation mechanism may include a rotation wheel housing the one or more control blocks the rotation wheel coupled with the control blocks to assist in rotation and allow for longitudinal movement of the one or more control blocks along an axis. The rotation wheel may be any structure that may be manipulated by the user to rotate the one or more assemblies. The rotation wheel may be generally ringed shaped, square shaped, rod shaped, multi-sided shape, or a combination thereof. Preferably, the rotation wheel may have an inside surface forming a space where the control blocks may be coupled and the rotation wheel may have an outside surface which may be manipulated by the user. The rotation wheel may have a plurality of slots on the inside surface. The plurality of slots inside the rotation wheel may be any size and shape so that the one or more tabs extending laterally from the spool control block are coupled to the rotation wheel. The rotation wheel may have an outside surface with a plurality of indentations. The plurality of indentations may allow for a thumb or finger to grip and manipulate the rotation wheel and spin the rotation wheel around the longitudinal axis of the stylet. The rotation wheel may have a groove on the distal side of the rotation wheel. The groove on the distal side of the rotation wheel may span the circumference of the rotation wheel. The groove may allow for the rotation wheel to be restrained in the hand piece. The groove may allow for the rotation wheel to be restrained in a web of the housing structure. The groove may restrain the motion of the rotation wheel to only be rotated around a longitudinal axis of the stylet and not allow for the rotation wheel to be moved in a longitudinal or lateral direction.

The present teachings provide a device including one or more of the following features: wherein one of the one or more assemblies is a cutting assembly, and the one or more support rods is one or more blade support rods; wherein the one or more functional attachments is a blade attached to the one or more blade support rods, and the proximal end region of the one or more blade support rods being in communication with the one or more actuating mechanisms; wherein one of the one or more assemblies is a gripping assembly, and the one or more support rods is one or more jaw support rods, or the hollow tube or both; wherein the one or more functional attachments is one or more jaws and one or more opposing jaws that are attached to the one or more jaw support rods or the hollow tube or both, and the proximal end region of the one or more jaw support rods is in communication with the one or more actuating mechanisms; wherein one of the one or more assemblies is a gripping assembly, and the one or more support rods is one or more jaw support rods, or the hollow tube or both; wherein the one or more functional attachments is one or more jaws and one or more opposing jaws that are attached to the one or more jaw support rods or the hollow tube or both, and the proximal end region of the one or more jaw support rods is in communication with the one or more actuating mechanisms; wherein one of the one or more assemblies is a cutting assembly, and the one or more support rods is one or more blade support rods; wherein the one or more functional attachments is one or more blades attached to the one or more blade support rods, and the proximal end region of the one or more blade support rods being in communication with the one or more actuating mechanisms; wherein the one or more assemblies is a combination gripping assembly and cutting assembly, and the one or more support rods is one or more blade support rods and another of the one or more support rods is one or more jaw support rods or the hollow tube, or both; wherein the one or more functional attachments is a combination of the one or more jaws and the one or more opposing jaws and the one or more blades, the one or more functional attachments being attached to the one or more support rods, and the proximal end region of the one or more support rods being in communication with the one or more actuating mechanisms; wherein the one or more levers have either the one or more cam fingers extending from the one or more levers, or the one or more arms extending from the one or more levers, or both, and the one or more levers being in communication with the one or more assemblies, the movement of the one or more levers causing actuation of the one or more functional attachments; wherein the single cam finger actuates the slidable joint on a single side of the control block, the single cam finger extending from the one or more levers being configured to be assembled by placing and/or advancing the single cam finger along the assembly direction so that the single cam finger rests against the control block and is in communication with the one or more support rods; wherein the cavity is a cavity in the top portion, the bottom portion, or both and the stylet and one or more levers are connected first to the top portion or the bottom portion and then the top portion or the bottom portion respectively covers and closes the cavity; wherein the assembly direction is a direction normal to a plane bisecting the hand piece; wherein the stylet is placed into the bottom portion of the hand piece along the assembly direction before the one or more levers, or after the one or more levers, and wherein the top portion of the hand piece is placed over the one or more levers and the stylet so that the top portion is connected to the bottom portion of the hand piece thereby covering and closing the stylet and the one or more levers in the cavity; wherein the bottom portion and the top portion are separated by a plane that extends through the hand piece and a line defining the direction of assembly extends normal to the plane; wherein the assembled stylet includes: a hollow tube; one or more opposing jaws; one or more jaw anchor support rods; a blade; one or more blade support rods; one or more control blocks; a rotation wheel; a bearing fitting; a bias device, a shuttle with a socket and a travel pin, or a combination thereof; wherein one or more levers have an arm with a camming slot to receive the travel pin of the shuttle on one side of the stylet, wherein the camming slot is placed onto the travel pin of the shuttle without repositioning the stylet, or wherein the travel pin of the shuttle is placed into the camming slot without repositioning the arm with the camming slot; wherein one or more levers have a single cam finger that connects with the one or more control blocks on one side of the stylet, and wherein the stylet can be placed into position without repositioning the single cam finger, or wherein the single cam finger can be placed into position without repositioning the stylet.

The process steps listed herein may be performed in virtually any order. The process to assemble the forceps may be any combination of steps that may allow for the necessary parts and sub-assemblies to be placed into position in a top-down assembly. The process may be any combination of steps that may allow top-down assembly without repositioning any parts or sub-assemblies already in place. The process may be any combination of steps that may allow for the top-down assembly along an assembly direction that is normal to a bisecting plane. The process may include one or more of the following steps performed in virtually any order unless specifically indicated. The process of assembling of the forceps may include the step of combining parts to form the stylet sub-assembly, for example the hollow tube, the one or more assemblies, the one or more control blocks, the rotation wheel, the bearing fitting, a return device and a shuttle. The assembly of the forceps may include the step of placing the stylet sub-assembly and the one or more levers into the hand piece, in any order. The stylet sub-assembly and the one or more levers may be place into the hand piece along an assembly direction. The one or more levers may be placed along the assembly line to have the one or more cam fingers, the camming slot, or both, be in contact with the one or more control blocks, the travel pin of the shuttle, or both. The bisecting plane as taught herein may bisect the hand piece along a center line to form two halves. The line normal to the bisecting plane may be perpendicular to one of the halves formed by the bisecting plane. The assembly direction may be any direction that allows the stylet sub-assembly and the one or more levers to be placed into one of the halves of the hand piece formed by the bisecting plane. The stylet sub-assembly may be placed into the hand piece first and the one or more levers second, or the one or more levers may be placed into the hand piece first and the stylet sub-assembly second. When the stylet sub-assembly may be placed into the hand piece first, the one or more levers may be placed in second without manipulating or repositioning the stylet sub-assembly. When the one or more levers may be placed into the hand piece first, the stylet sub-assembly may be placed in second without manipulating or repositioning the one or more levers. The assembly direction may be described as top-down or bottom-up when the device is lying flat on the side of the device. The method of assembly may include steps of attaching parts to other parts. The method of attachment may include, but is not limited to; using adhesives, molding, welding or other suitable means.

FIG. 1 illustrates forceps 2 including a hand piece 50 with a nose cone 4, and a vertical plane 100 bisecting the hand piece 50, extending from the proximal end of the hand piece 50 to the distal end of the hand piece 50. The hand piece 50 is connected to a stylet 10 that is partially disposed in the hand piece 50. The hand piece 50 includes a clamp lever 66, a cut trigger lever 67, and a rotation wheel 82 for manipulating one or more features of the stylet 10. The clamp lever 66 and the cut trigger lever 67 are disposed partially inside the hand piece 50. The rotation wheel 83 is restrained to only axial rotation by the hand piece 50.

Figure 2A:
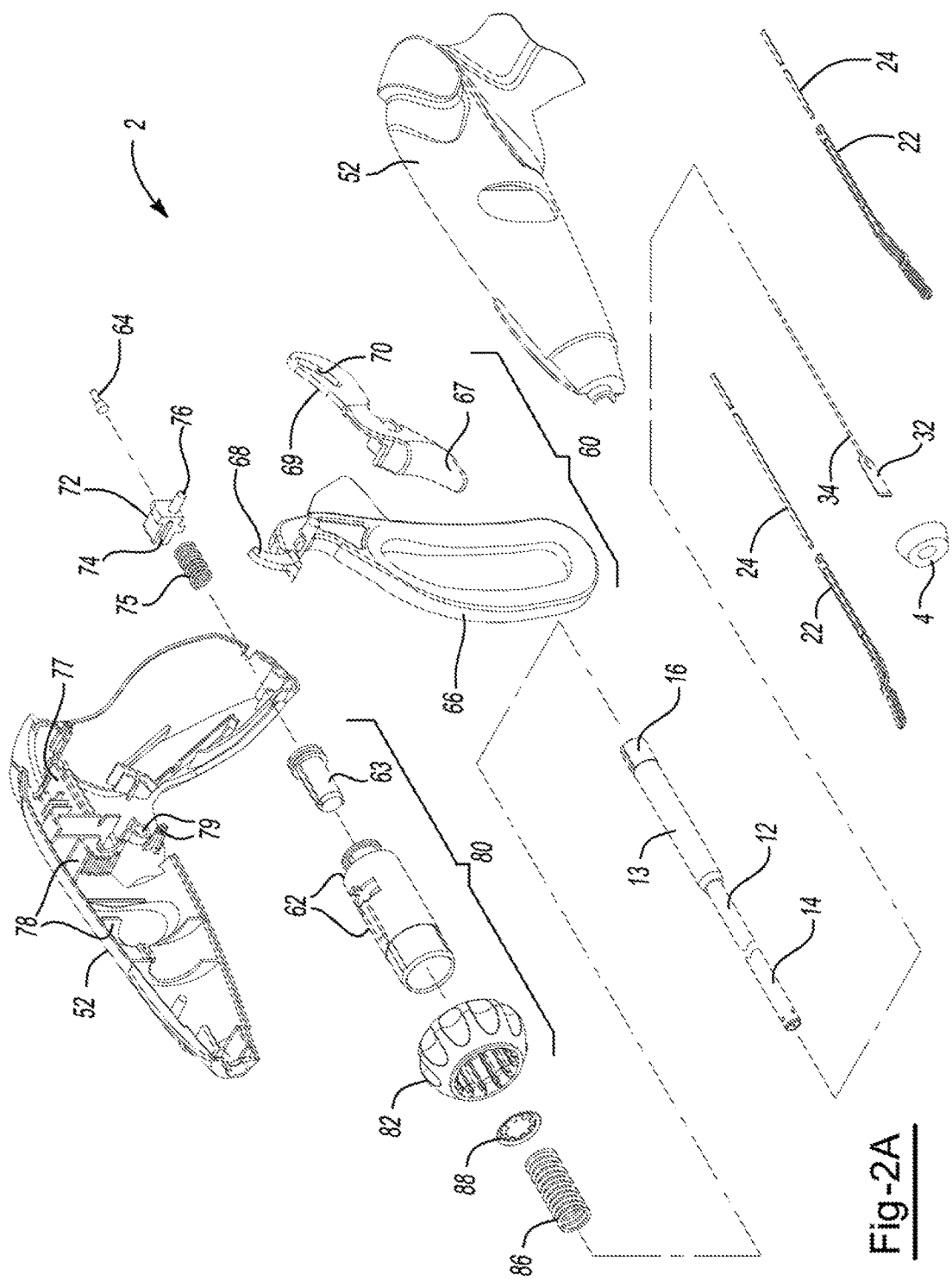
FIG. 2A illustrates an exploded view of another embodiment of the forceps device.

FIG. 2A illustrates an exploded view of a forceps 2. The forceps 2 include a nose cone 4. The forceps 2 include jaws 22 and jaw support rods 24 that are attached to each other to form a gripping mechanism. The forceps 2 include a blade 32 and a blade support rod 34 that may be attached to each other to form a cutting mechanism. The gripping mechanism and the cutting mechanism may be inserted through a hollow tube 12 with a tapered overmolding portion 13 forming a stylet 10. The hollow tube 12 has a distal end 14 and a proximal end 16. A return mechanism 86, a stopping device 88, a rotation wheel 82, a spool control block 62, an anchor control block 63 are all part the rotation mechanism 80. The stylet 10 may be inserted through the rotation mechanism 80. At the end of the blade support rod 34 extended through the rotation mechanism 80 includes a bias device 75, a shuttle 72, housing a socket 74, and a bearing fitting 64. The stylet 10, the rotation mechanism 80, and the bias device 75, the shuttle 72, the socket 74, form the stylet sub-assembly. The forceps 2 includes a clamp lever 66 with a single cam finger 68, and a cut trigger lever 67 with an arm 69 and a camming slot 70. The clamp lever and cut trigger lever may be attached to one or more pivot axes 79. The clamp lever 66, and the cut trigger lever 67, the shuttle 72 and socket 74, the bearing fitting 64 and a travel pin 76 comprise the actuation mechanism 60. The forceps 2 includes two housing structures 52. The housing structures 52 include web structures 78, one or more pivot axes 79, and one or more guide ridges 77.

Figure 2B:
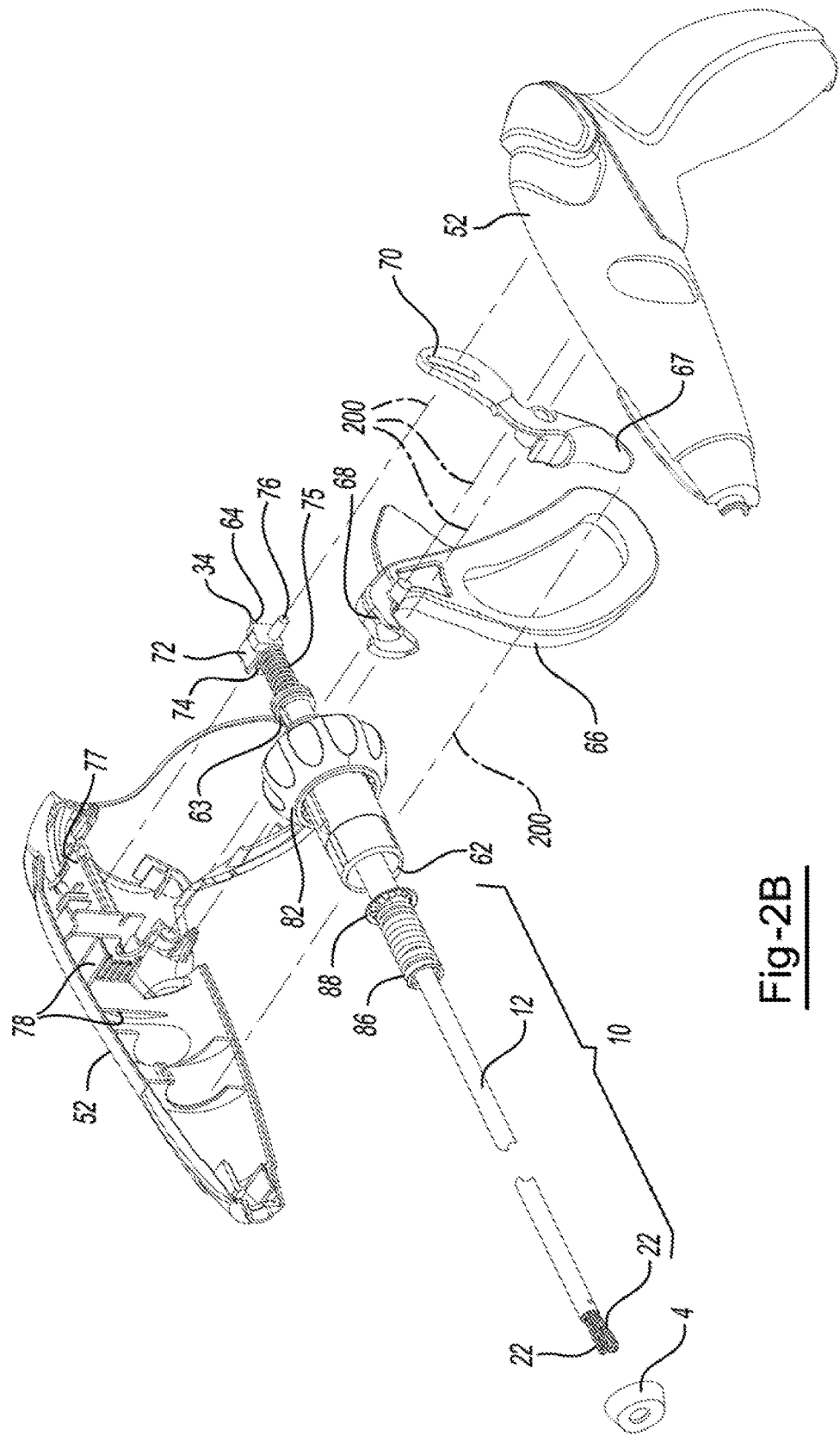
FIG. 2B illustrates an exploded view of the forceps device in FIG. 2A being assembled.

FIG. 2B illustrates an exploded view of the device in FIG. 2A being assembled along the assembly direction 200. The forceps 2 are assembled by attaching the jaws 22 to the jaw support rods 24 forming the gripping assembly, attaching the blade 32 to the blade support rod 34 to for the cutting assembly and inserting the gripping assembly and the cutting assembly into the hollow tube 12 forming the stylet 10. The proximal end of the hollow tube 16 disposed in the hand piece 50. The stylet 10 is inserted through a return mechanism 86, a stopping device 88, a rotation wheel 82, a spool control block 62, an anchor control block 63 all comprising the rotation mechanism 80. At the end of the blade support rod 34 inserted through the rotation mechanism 80, there is a bias device 75 that is affixed to the blade support rod 34, a bearing fitting 64 attached to the blade support rod 34, shuttle 72 and a socket 74 housed by the shuttle 72 that fits over the bearing fitting 64. The stylet 10, the rotation mechanism 80, and the bias device 75, the bearing fitting 64, the shuttle 72 and socket 74, and the travel pin 76, all make up the stylet sub-assembly. The stylet sub-assembly may be placed into position in the housing structure 52 forming the bottom portion. The stylet sub-assembly is secured into place by the web structures 78 and by one or more guide ridges 77. The forceps 2 include a clamp lever 66 and a cut trigger lever 67 that may be placed into position along an assembly direction normal to the bisecting plane 100. The clamp lever 66 is placed into position along the assembly direction so that the single cam finger 68 is in communication with the spool control block 62. The cut trigger 67 is placed into position along the assembly direction so that the arm 69 and the camming slot 70 receive the travel pin 76 of the shuttle 72. The housing structure 52 that does not have the parts placed into position is then secured to the other housing structure 52 to form the complete hand piece 50.

Figure 2C:
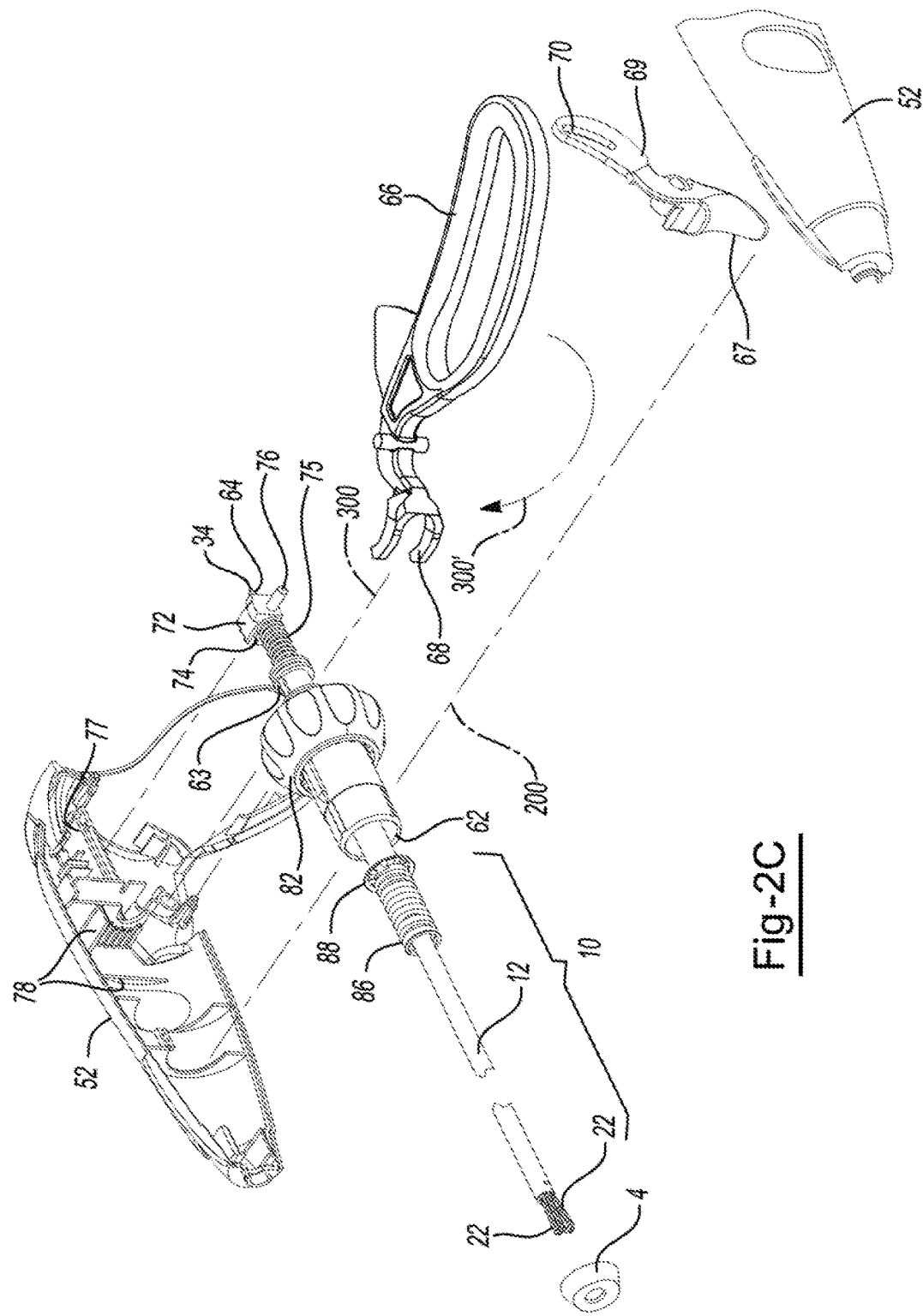
FIG. 2C illustrates an exploded view of the forceps device in FIG. 2A being assembled with a secondary assembly direction.
Figure 3:
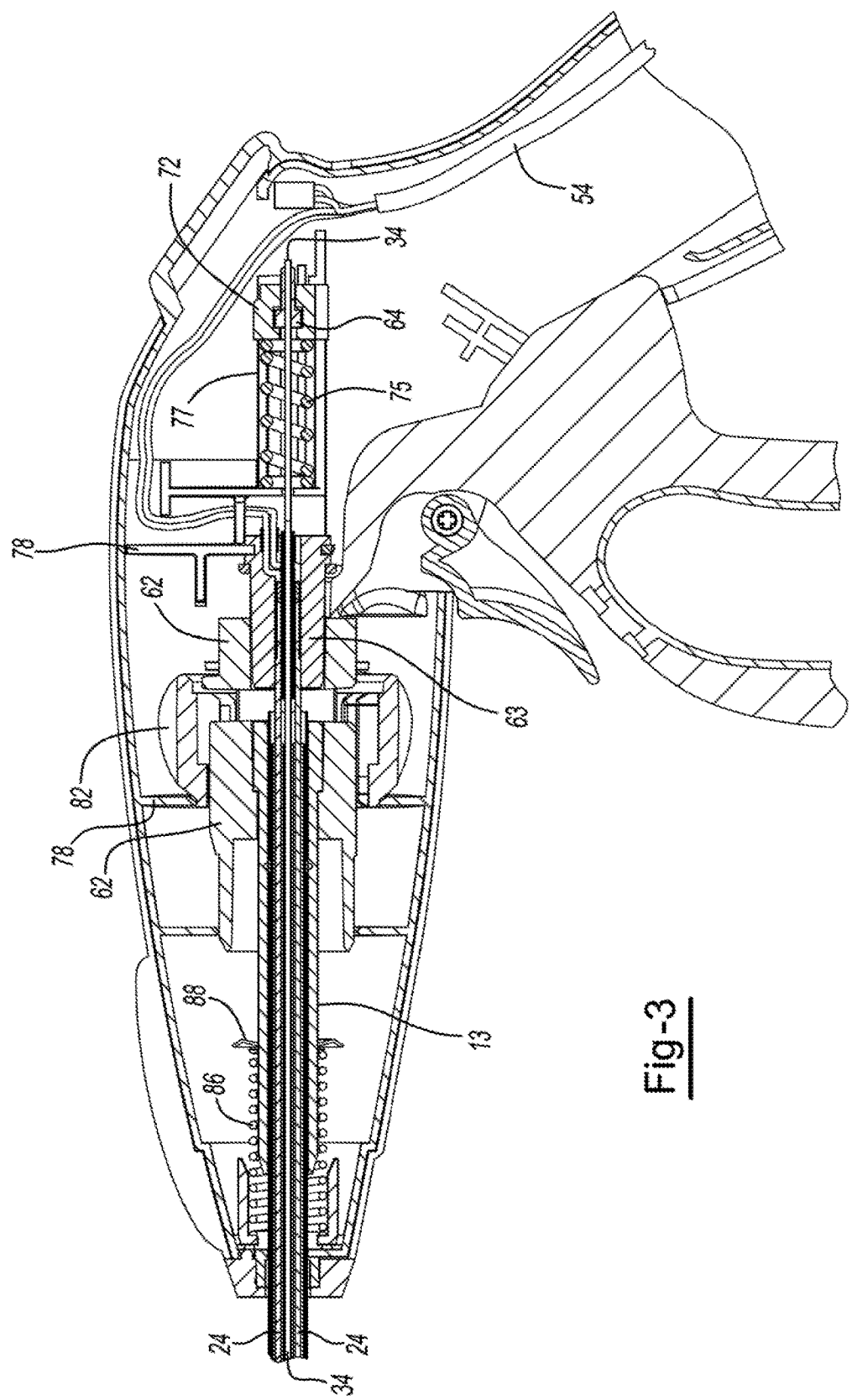
FIG. 3 illustrates a cross-sectional view of FIG. 1, along a plane (100)

FIG. 2C illustrates an exploded view of the device in FIG. 2A being assembled along an assembly direction 200. The one or more levers with one or more cam fingers being assembled along a primary assembly line 300 and including a secondary assembly direction 300' to rotate the one or more levers with two-sided cam finger or yoke into place consistent with top-down assembly. The forceps 2 are assembled by attaching the jaws 22 to the jaw support rods 24 forming the gripping assembly, attaching the blade 32 to the blade support rod 34 to for the cutting assembly and inserting the gripping assembly and the cutting assembly into the hollow tube 12 forming the stylet 10. The stylet 10 is inserted through a return mechanism 86, a stopping device 88, a rotation wheel 82, a spool control block 62, an anchor control block 63 all comprising the rotation mechanism 80. At the end of the blade support rod 34 inserted through the rotation mechanism 80, there is a bias device 75 that fits over the blade support rod 34, a bearing fitting 64 attached to the blade support rod 34, shuttle 72 and a socket 74 housed by the shuttle 72 that fits over the bearing fitting 64. The stylet 10, the rotation mechanism 80, and the bias device 75, the bearing fitting 64, the shuttle 72 and socket 74, and the travel pin 76, all make up the stylet sub-assembly. The stylet sub-assembly may be placed into position in the housing structure 52 forming the bottom portion. The stylet sub-assembly is secured into place by the web structures 78 and by one or more guide ridges 77. The forceps 2 include a clamp lever 66 and a cut trigger lever 67 that may be placed into position along an assembly direction normal to the bottom portion of the housing structures 52. The clamp lever 66 is placed into position along the primary assembly line 300 while positioned at an angle so that the two-sided cam finger or yoke 68 fits over the one or more control blocks and rotated into position along a secondary assembly direction 300' consistent with the assembly direction 200. The two-sided cam finger, or yoke 68 is in communication with the spool control block 62 and is rotated along the secondary assembly direction 300' so that the length of the clamp lever 66 is placed into position along the assembly direction 200. The cut trigger 67 is placed into position along the assembly direction so that the arm 69 and the camming slot 70 receive the travel pin 76 of the shuttle 72. The housing structure 52 that does not have the parts placed into position FIG. 3 illustrates a cross-sectional view of FIG. 1, cut along the bisecting plane 100. The forceps 2 of FIG. 3 include the jaw support rods 24, and the blade support rods 34 extending into the hand piece 50. The forceps 2 include a return mechanism 86 and a stopping device 88 inside the distal end of the hand piece 50, surrounding the tapered overmolding portion 13 of the stylet 10. The stylet 10 extends into the spool control block 62, through the spool control block 62 an into the anchor control block 63. The blade support rod 34 extends through the anchor control block 63 and into of the one or more guide ridges 77 where the end of the blade support rod 34 extends through a bias device 75, and a bearing fitting 64 that is received by a socket 74 housed by a shuttle 72. The spool control block 62 and the anchor control block 63 are both coupled to a rotation wheel 82. The spool control block 62 may be affixed to the overmold portion 13 so that there is no relative axial motion between the two. The rotation wheel 82, the spool control block 62 and the anchor control block 63 are secured in the housing structures 52 by web structures 78. The forceps 2 include a power cord 54 disposed of in the anchor control block 63 and connected to the jaw support rods 24. The power cord 54 exits out the bottom of the hand piece 50.

Figure 4A:
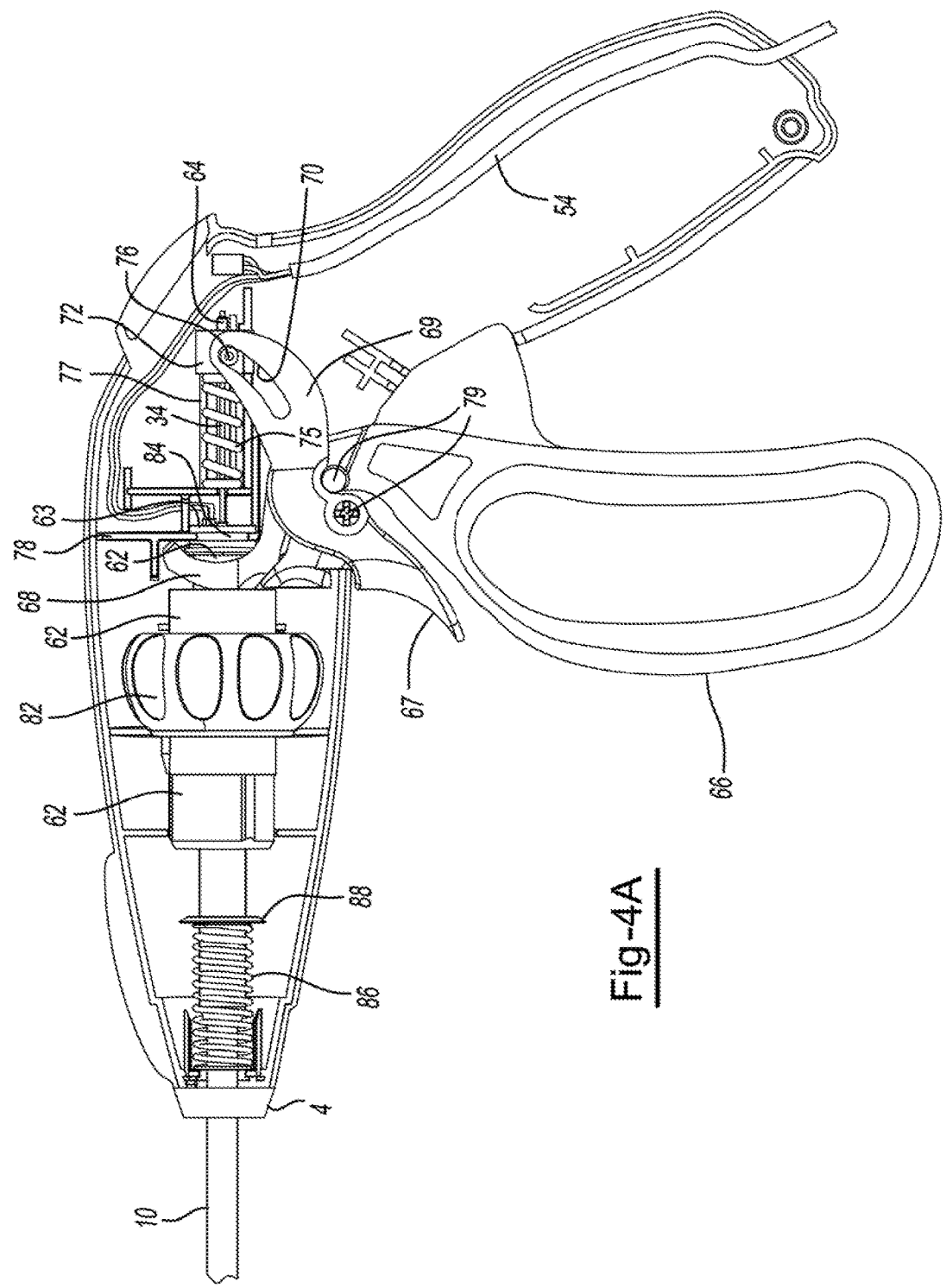
FIG. 4A illustrates a side view of the forceps device of FIG. 1 with the top cover removed and both triggers in the neutral position.

FIG. 4A illustrates a side view of the forceps 2 with the top portion of the housing structures 50 removed and both triggers in the neutral position. The forceps 2 include a nose cone 4 at the distal end of the hand piece 50. The forceps 2 include a stylet 10 extending through the nose cone 4, through the tapered over molding portion 13 of the hollow tube 12 through the return mechanism 86, through the stopping device 88, through the spool control block 62, the rotation wheel 82, into the anchor control block 63. The blade support rod 34 of the stylet 10 extends through the anchor control block 63, through a bias device 75, and into the one or more guide ridges 77 where it is attached to a bearing fitting 64 and housed by a shuttle 72 and socket 74. The clamp lever 66 is attached to the hand piece 50 at one or more pivot axes 79 and the single cam finger 68 is in communication with the spool control block 62. The clamp lever 66 is in the neutral position. The cut trigger lever 67 is attached the hand piece 50 at one or more pivot axes 79, and the arm 69 and camming slot 70 receive the travel pin 76 of the shuttle 72. The cut trigger lever 67 is in the neutral position.

Figure 4B:
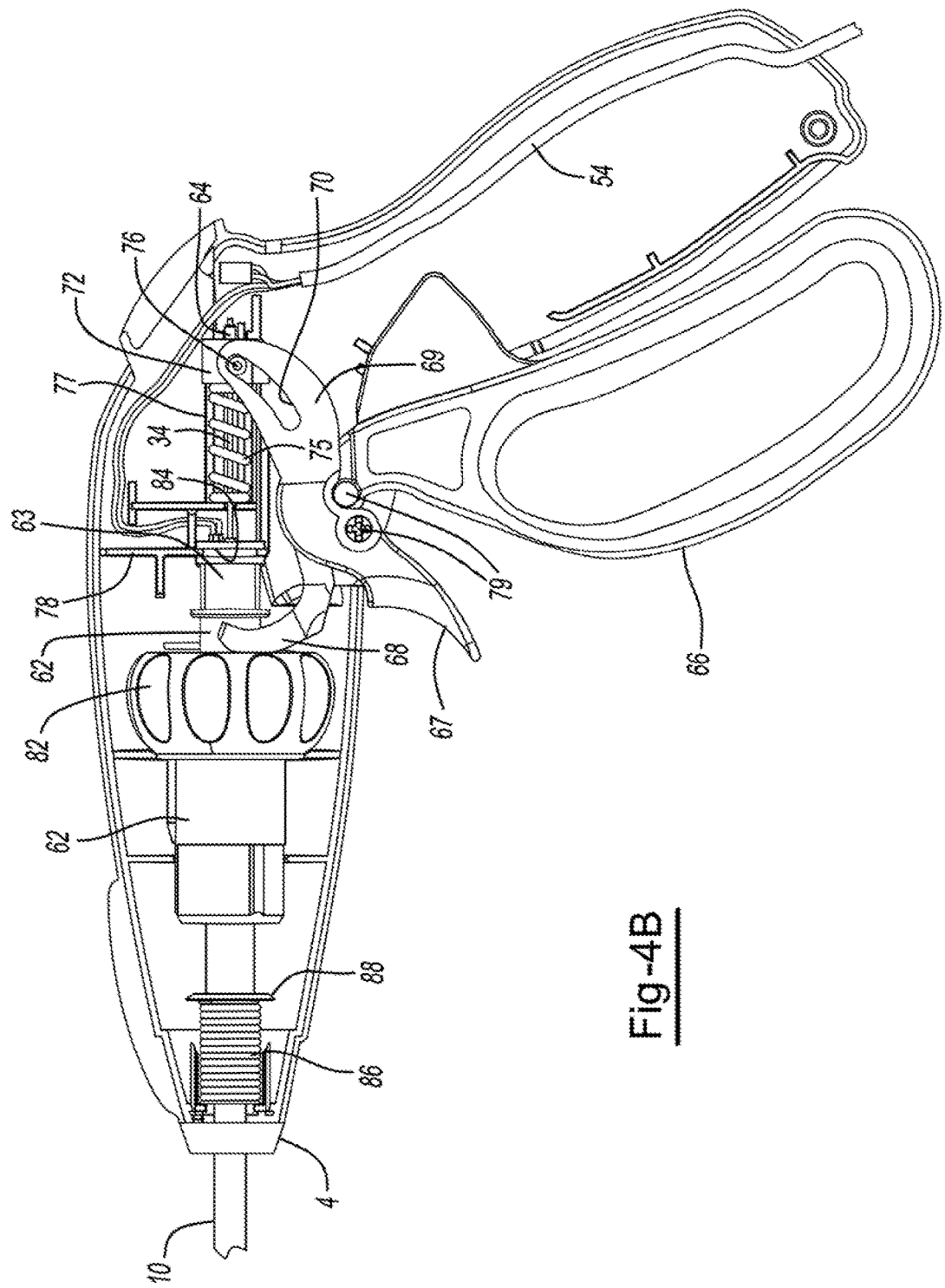
FIG. 4B illustrates a side view of the forceps device of FIG. 1 with the top cover removed and with one trigger retracted.

FIG. 4B illustrates a side view of the forceps 2 with the top portion of the housing structures 50 removed, the clamp lever 66 in a retracted position and the cut trigger lever 67 in the neutral position. The forceps 2 include a nose cone 4 at the distal end of the hand piece 50. The forceps 2 include a stylet 10 extending through the nose cone 4, through the tapered over molding portion 13 of the hollow tube 12 through the return mechanism 86, through the stopping device 88, through the spool control block 62, the rotation wheel 82, into the anchor control block 63. The blade support rod 34 of the stylet 10 extends through the anchor control block 63, through a bias device 75, and into the one or more guide ridges 77 where it is attached to a bearing fitting 64 and housed by a shuttle 72 and socket 74. The clamp lever 66 is attached to the hand piece 50 at one or more pivot axes 79 and the single cam finger 68 is in communication with the spool control block 62. The clamp lever 66 is in the retracted position. The cut trigger lever 67 is attached the hand piece 50 at one or more pivot axes 79, and the arm 69 and camming slot 70 receive the travel pin 76 of the shuttle 72. The cut trigger lever 67 is in the neutral position.

Figure 4C:
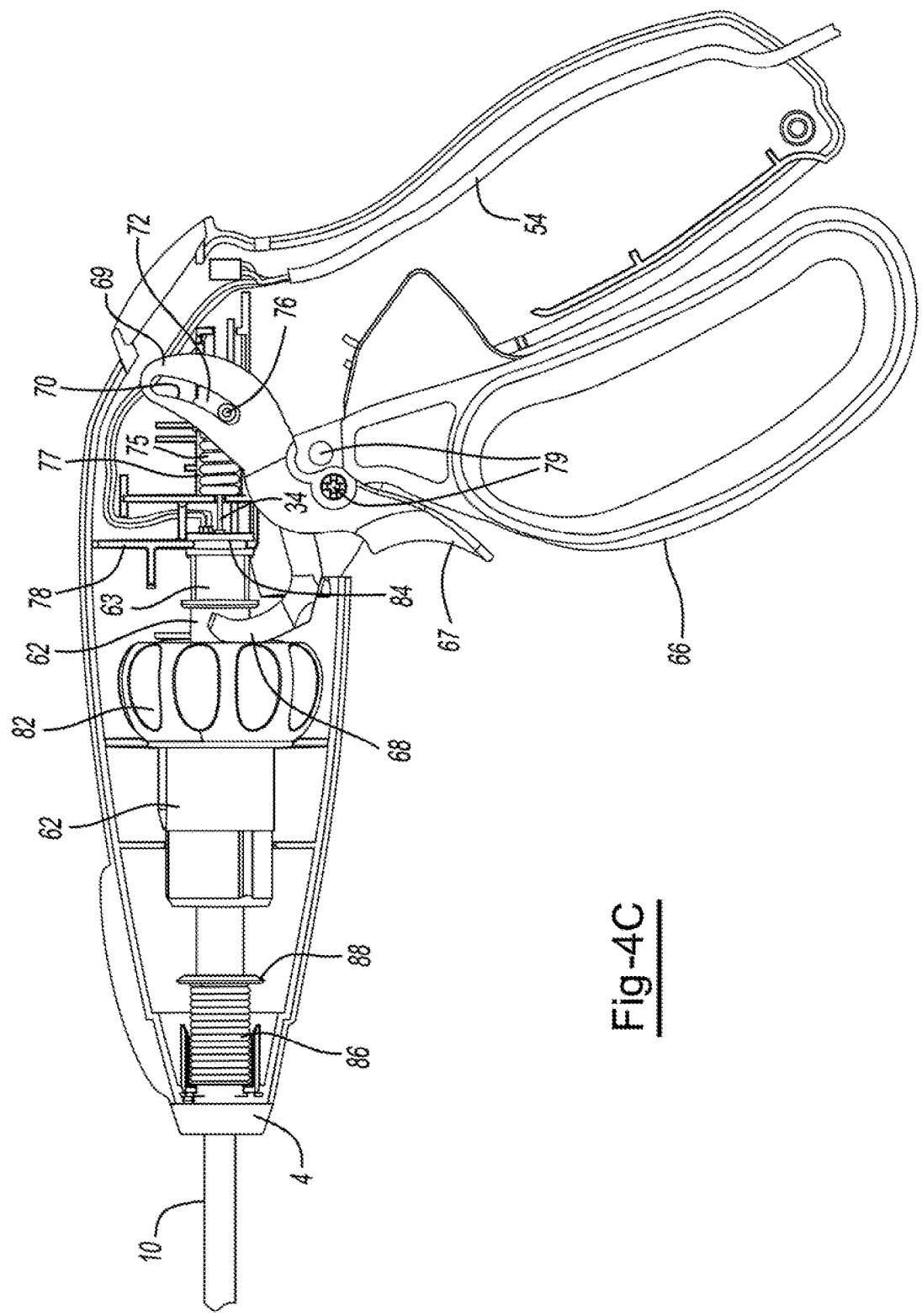
FIG. 4C illustrates a side view of the forceps device of FIG. 1 with the top cover removed and with both triggers retracted.

FIG. 4C illustrates a side view of the forceps 2 with the top portion of the housing structures 50 removed, the cut trigger lever 67 in a retracted position and the clamp lever 66 in the retracted position. The forceps 2 include a nose cone 4 at the distal end of the hand piece 50. The forceps 2 include a stylet 10 extending through the nose cone 4, through the tapered over molding portion 13 of the hollow tube 12 through the return mechanism 86, through the stopping device 88, through the spool control block 62, the rotation wheel 82, into the anchor control block 63. The blade support rod 34 of the stylet 10 extends through the anchor control block 63, through a bias device 75, and into the one or more guide ridges 77 where the blade support rod 34 is attached to a bearing fitting 64 that is housed in a shuttle 72 and socket 74. The clamp lever 66 is attached to the hand piece 50 at one or more pivot axes 79 and the single cam finger 68 is in communication with the spool control block 62. The clamp lever 66 is in the retracted position. The cut trigger lever 67 is attached the hand piece 50 at one or more pivot axes 79, and the arm 69 and camming slot 70 receive the travel pin 76 of the shuttle 72. The cut trigger lever 67 is in the retracted position.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A forceps comprising:
   a) a stylet having a distal end and a proximal end region, the stylet comprising:
      (i) a hollow tube having a proximal end region and a longitudinal axis;
      (ii) one or more assemblies that are extendable through the hollow tube, the one or more assemblies comprising;
         1) one or more support rods having a distal end and a proximal end region;
         2) one or more functional attachments at the distal end of the one or more support rods;
   b) a hand piece comprising,
      (i) one or more housing structures defining a cavity that houses the proximal end region of the stylet;
      (ii) one or more actuating mechanisms in communication with the proximal end region of the stylet, the one or more actuating mechanisms comprising:
         1) a bearing fitting located on the proximal end region of the stylet, the bearing fitting being both rotatably and axially moveable and having one of the one or more support rods extending therethrough;
         2) a shuttle in communication with the bearing fitting, the shuttle constrained by a plurality of guide ridges attaches to the one or more housing structures so that the shuttle is movable along a longitudinal axis and restricted from rotational movement around the longitudinal axis;
         3) a socket housed by the shuttle, the socket receiving the bearing fitting so that the bearing fitting is rotatable relative to the shuttle; and
         4) one or more levers in communication with the stylet so that movement of the one or more levers causes movement of the hollow tube or movement of the one or more assemblies; and
      wherein the movement of the hollow tube and the movement of the one or more assemblies are relative to each other.

2. The forceps of claim 1, wherein the forceps comprises a rotation mechanism comprising:
   (a) a rotation wheel held by the one or more housing structures;
   (b) one or more control blocks coupled to the rotation wheel; and
   (c) the one or more assemblies being in communication with the one or more control blocks so that rotating the rotation wheel thereby rotates the stylet around the longitudinal axis of the hollow tube, or rotates the one or more assemblies around the longitudinal axis of the hollow tube, or both.

3. The forceps of claim 2, wherein one or more arms extend from the one or more levers, the one or more arms having one or more camming slots, a travel pin extending outward from the shuttle and received by the one or more camming slots, the one or more assemblies being in communication with the shuttle, the movement of the one or more levers causing actuation of the one or more assemblies.

4. The forceps of claim 2, wherein one or more cam fingers extend from the one or more levers, the one or more cam fingers being in communication with the shuttle so that the movement of the one or more levers causes actuation of the one or more assemblies.

5. The forceps of claim 2, wherein one of the one or more assemblies is a cutting assembly, and the one or more support rods is one or more blade support rods; and
   wherein the one or more functional attachments is a blade attached to the one or more blade support rods, and the proximal end region of the one or more blade support rods being in communication with the one or more actuating mechanisms.

6. The forceps of claim 5, wherein the one or more support rods include one more jaw support rods and the one or more functional attachments includes opposing jaws having a gap formed therebetween;
   wherein the proximal end region of the one or more blade support rods extends through the bearing fitting; and
   wherein the blade is extendable into and retractable from the gap between the opposing jaws and through the hollow tube.

7. The forceps of claim 2, wherein one of the one or more assemblies is a gripping assembly, and the one or more support rods is one or more jaw support rods, or the hollow tube or both; and
   wherein the one or more functional attachments is one or more jaws and one or more opposing jaws that are attached to the one or more jaw support rods or the hollow tube or both, and the proximal end region of the one or more jaw support rods is in communication with the one or more actuating mechanisms.

8. The forceps of claim 7, wherein the distal end of the one or more jaw support rods extends out of a distal end of the hollow tube opposite the proximal end region of the hollow tube; and
   wherein the proximal end region of the one or more jaw support rods extends from the proximal end region of the hollow tube and is secured to at least one of the one or more control blocks.

9. The forceps of claim 2, wherein the one or more assemblies include a gripping assembly and a cutting assembly, the gripping assembly and the cutting assembly having one or more of the one or more support rods, a blade attachment, and two or more jaw attachments.

10. The forceps of claim 9, wherein one or more cam fingers are extending from the one or more levers, the one or more cam fingers being in communication with the one or more assemblies, the movement of the one or more cam fingers causing actuation of the one or more assemblies.

11. The forceps of claim 2, wherein the one or more control blocks include one or more spool control blocks and an outside of the one or more spool control blocks is coupled with an inside of the rotation wheel to allow for rotation and longitudinal movement along the longitudinal axis.

12. The forceps of claim 11, wherein the one or more control blocks include one or more anchor control blocks located within and coupled to the one or more spool control blocks so that rotation of the one or more spool control blocks causes rotational movement of the one or more anchor control blocks.

13. The forceps of claim 11, wherein the hollow tube includes an overmolded portion at the proximal end region which is tapered and is located partially within the one or more spool control blocks and transfers axial movement from the one or more control blocks to the hollow tube.

14. The forceps of claim 12, wherein the one or more anchor control blocks include one or more fins extending from an outside surface which are coupled with one or more grooves on an inside surface of the one or more spool control blocks.

15. The forceps of claim 12, wherein the one or more housing structures include one or more web structures which restrain the one or more anchor control blocks to prevent axial movement and allow for axial rotation so that the one or more spool control blocks slide over an outside of the one or more anchor control blocks.

16. The forceps of claim 12, wherein the one or more support rods include one or more blade support rods and the one or more functional attachments include a blade attached to the one or more blade support rods; and
   wherein the one or more blade support rods extend through the one or more anchor control blocks into the bearing fitting.

17. The forceps of claim 16, wherein the one or more blade support rods extend through a bias device and into the bearing fitting and the bias device returns the one or more blade support rods back into a neutral position after the one or more blade support rods have been actuated by at least one of the one or more actuating mechanisms.

18. The forceps of claim 17, wherein the bias device is located between the one or more anchor control blocks and the bearing fitting.

19. The forceps of claim 1, wherein the hollow tube extends through a return mechanism and a stopping device;
   wherein the return mechanism biases the hollow tube to a resting position so that when the hollow tube is actuated and released from actuation the hollow tube returns back to the resting position; and
   wherein the stopping device allows for the return mechanism to remain stationary at one end while applying force at an opposite end in an opposite direction.

20. The forceps of claim 1, wherein rotation of the one or more assemblies in independent of the hollow tube.

* * * * *